(12) United States Patent
Mayer

(10) Patent No.: US 12,324,618 B2
(45) Date of Patent: Jun. 10, 2025

(54) ABLATION PROBE

(71) Applicant: Erbe Elektromedizin GmbH, Tuebingen (DE)

(72) Inventor: Volker Mayer, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 448 days.

(21) Appl. No.: 17/004,606

(22) Filed: Aug. 27, 2020

(65) Prior Publication Data

US 2021/0068894 A1  Mar. 11, 2021

(30) Foreign Application Priority Data

Sep. 5, 2019  (EP) ..................................... 19195658

(51) Int. Cl.
*A61B 18/12* (2006.01)
*A61B 18/14* (2006.01)
*A61B 18/00* (2006.01)

(52) U.S. Cl.
CPC . *A61B 18/1492* (2013.01); *A61B 2018/00011* (2013.01); *A61B 2018/00077* (2013.01); *A61B 2018/00172* (2013.01); *A61B 2018/00577* (2013.01)

(58) Field of Classification Search
CPC ...... A61B 18/1492; A61B 2018/00011; A61B 2018/00077; A61B 2018/00172; A61B 2018/00577; A61B 2018/00095; A61B 2018/00101
See application file for complete search history.

(56) References Cited

U.S. PATENT DOCUMENTS 3,485,234 A   12/1969  Stevens
5,899,898 A    5/1999  Arless et al.
(Continued)

FOREIGN PATENT DOCUMENTS

CN   108135656 A   6/2018
DE     2945607 A1   5/1981
(Continued)

OTHER PUBLICATIONS

Extended European Search Report dated Mar. 13, 2020, in corresponding European Application No. 19195658.0, with machine English translation (11 pages).
(Continued)

*Primary Examiner* — Daniel W Fowler
(74) *Attorney, Agent, or Firm* — Fitch, Even, Tabin & Flannery LLP

(57) ABSTRACT

A probe that is particularly usable as a radio frequency ablation probe and comprises an inner cooling in order to keep the at least one electrode at the tissue wet and to avoid excessive heating. In the area of the electrode the hose wall of the hose supporting the electrode comprises an increased heat conductivity, whereas apart from that it has a comparably low heat conductivity outside of the electrode carrying distal end section. The increase of the heat conductivity in the distal end section can be achieved by reduction of the wall thickness, by selection of a suitable plastic, by arrangement of heat transfer bodies in the hose wall or by a combination of two or more of these features.

17 Claims, 5 Drawing Sheets

(56) References Cited

U.S. PATENT DOCUMENTS

| | | | |
|---|---|---|---|
| 6,475,214 B1* | 11/2002 | Moaddeb | A61B 18/1492 606/41 |
| 6,939,350 B2 | 9/2005 | Phan | |
| 2003/0171742 A1* | 9/2003 | Mihalik | A61M 25/0029 606/22 |
| 2003/0195503 A1 | 10/2003 | Jain et al. | |
| 2005/0055019 A1* | 3/2005 | Skarda | A61B 18/1492 606/41 |
| 2009/0171343 A1 | 7/2009 | Paul et al. | |
| 2012/0109116 A1* | 5/2012 | Asconeguy | A61B 18/02 606/21 |
| 2012/0197243 A1* | 8/2012 | Sherman | A61B 18/12 606/32 |
| 2013/0190754 A1 | 7/2013 | Paul et al. | |
| 2013/0281997 A1* | 10/2013 | Davie | A61B 18/02 606/32 |
| 2014/0228831 A1* | 8/2014 | Fischer | A61B 18/02 606/20 |
| 2015/0250982 A1* | 9/2015 | Osypka | A61B 18/02 606/108 |
| 2018/0132740 A1* | 5/2018 | Clark | A61B 5/283 |
| 2018/0214045 A1* | 8/2018 | Wittenberger | A61B 5/6853 |

FOREIGN PATENT DOCUMENTS

| | | |
|---|---|---|
| DE | 8504999 U1 | 8/1985 |
| DE | 8505999 U1 | 10/1985 |
| GB | 2236253 A | 4/1991 |
| JP | 2000-197641 A | 7/2000 |
| JP | 2004-73834 A | 3/2004 |
| JP | 2015095821 A | 5/2015 |
| RU | 2666115 C2 | 9/2018 |
| WO | 03/034932 A1 | 5/2003 |

OTHER PUBLICATIONS

Russian Patent Office; Office Action and Search Report in corresponding Russian Patent Application No. 2020128732/14, dated Aug. 22, 2023; 20 pages.
Japanese Patent Office; Notice of Reasons for Refusal in corresponding Japanese Patent Application No. 2020-148032, dated Nov. 8, 2023; 11 pages.
China National Intellectual Property Administration; Chinese Office Action in corresponding Chinese Patent Application No. 202010922879.0, dated Jan. 15, 2024; 11 pages.
China National Intellectual Property Administration; Search Report in corresponding Chinese Patent Application No. 202010922879.0, dated Jan. 15, 2024; 2 pages.
Japanese Patent Office; Decision of Refusal in corresponding Japanese Patent Application No. 2020-148032 dated Apr. 22, 2024, 8 pages.
National Intellectual Property Administration, P. R. China, Search Report in corresponding Chinese Patent Application No. 202010922879.0, dated Oct. 10, 2024; 2 pages.
National Intellectual Property Administration, P. R. China, Office Action in corresponding Chinese Patent Application No. 202010922879.0, dated Oct. 15, 2024; 12 pages.

\* cited by examiner

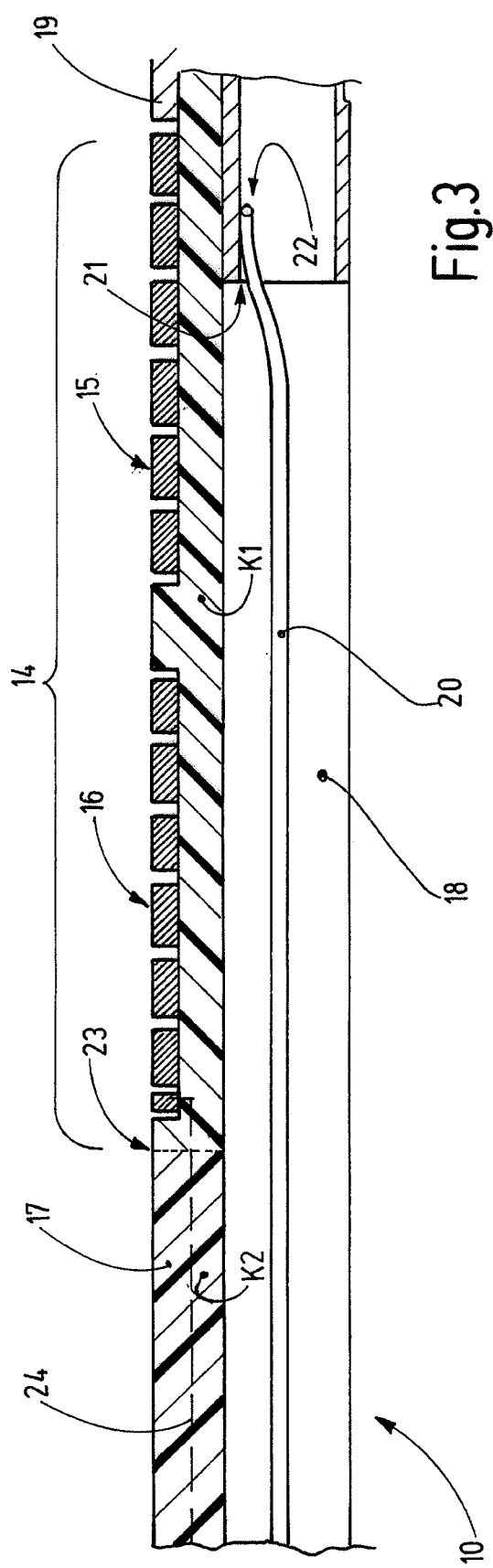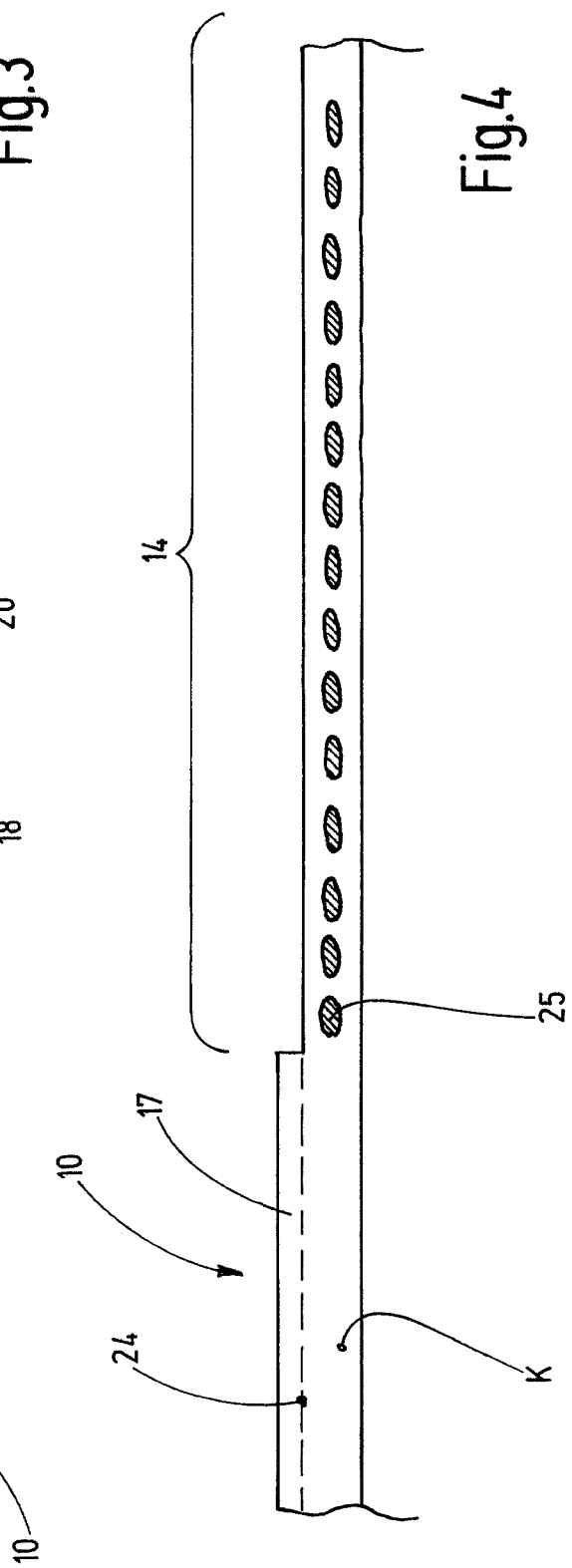

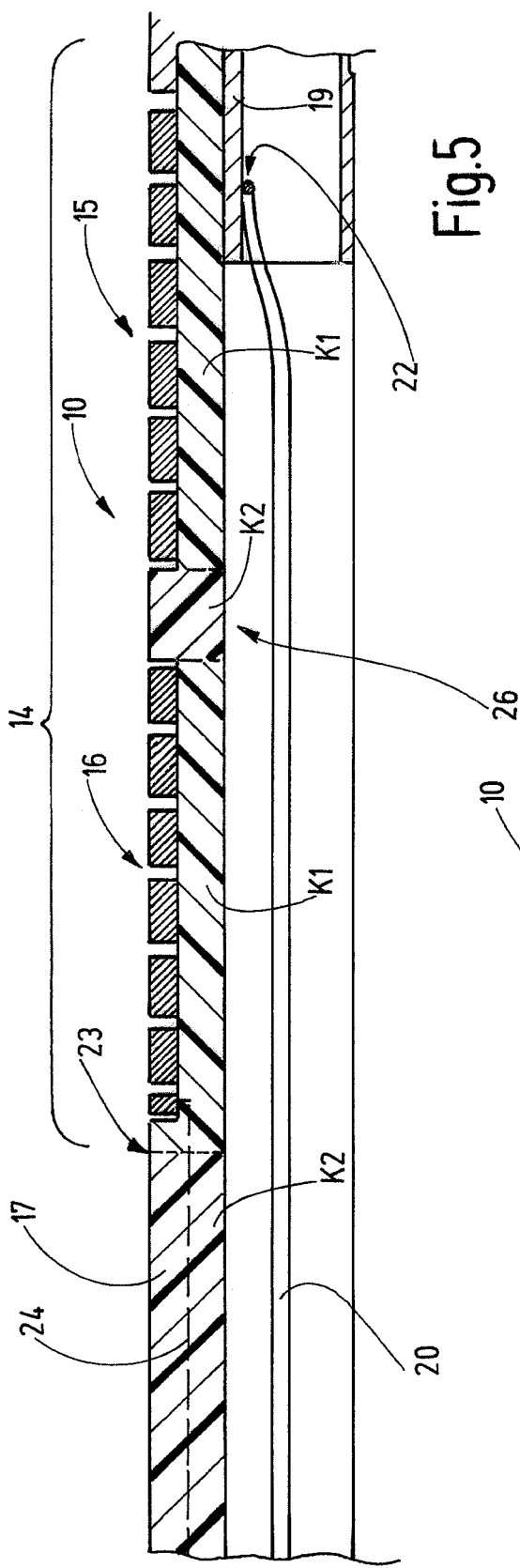
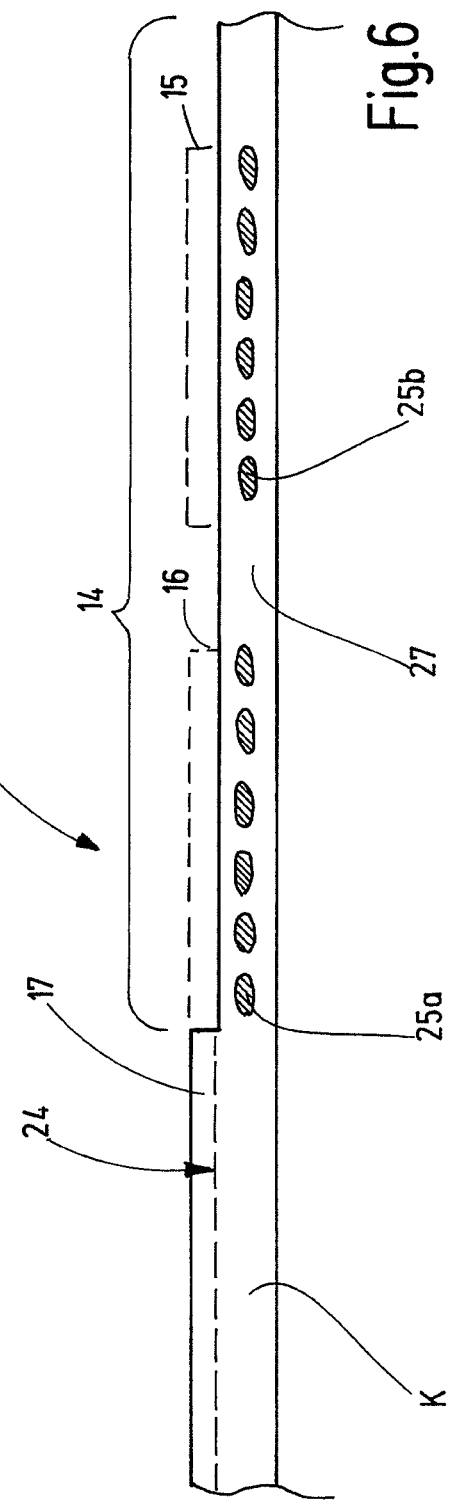

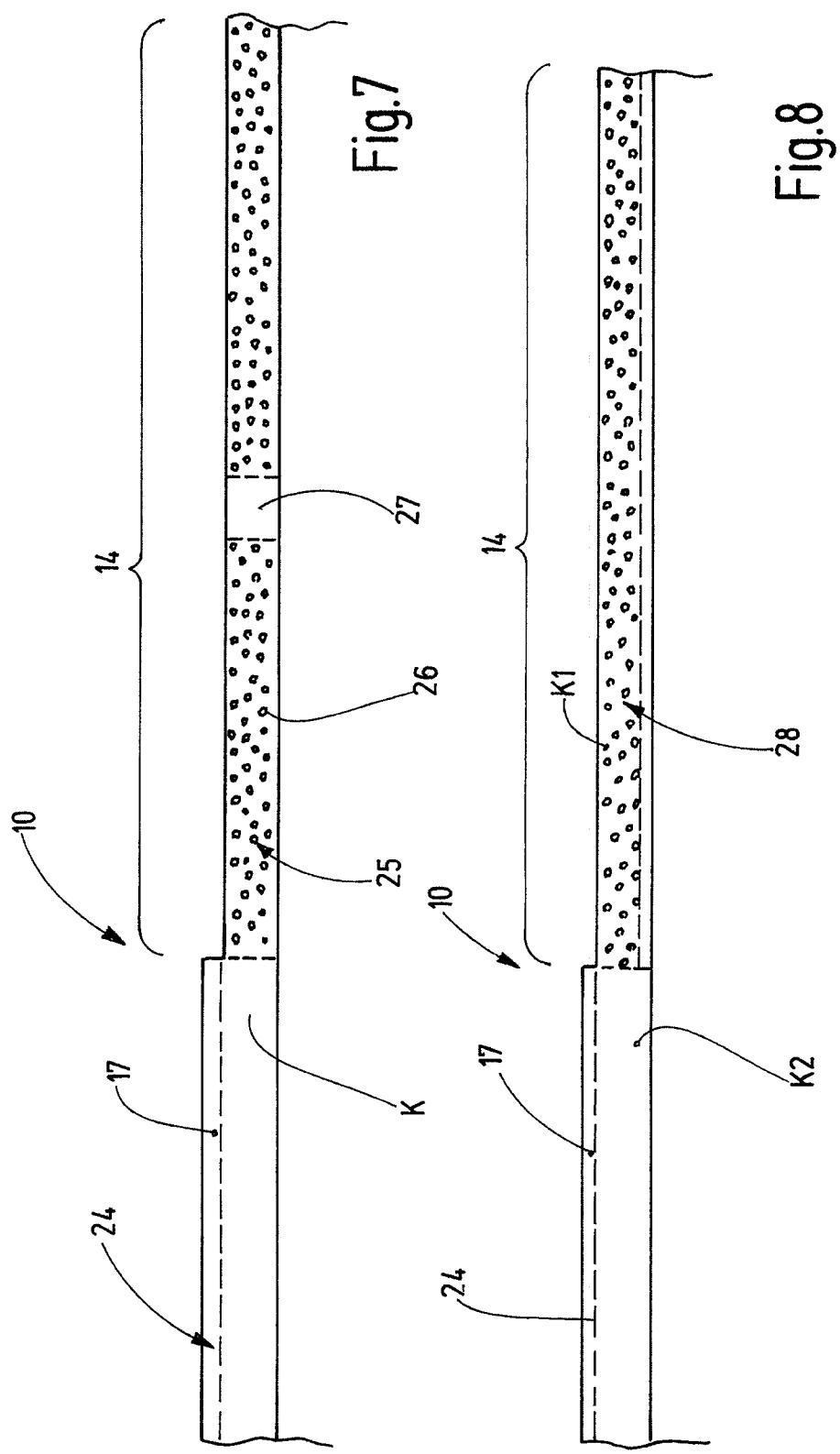

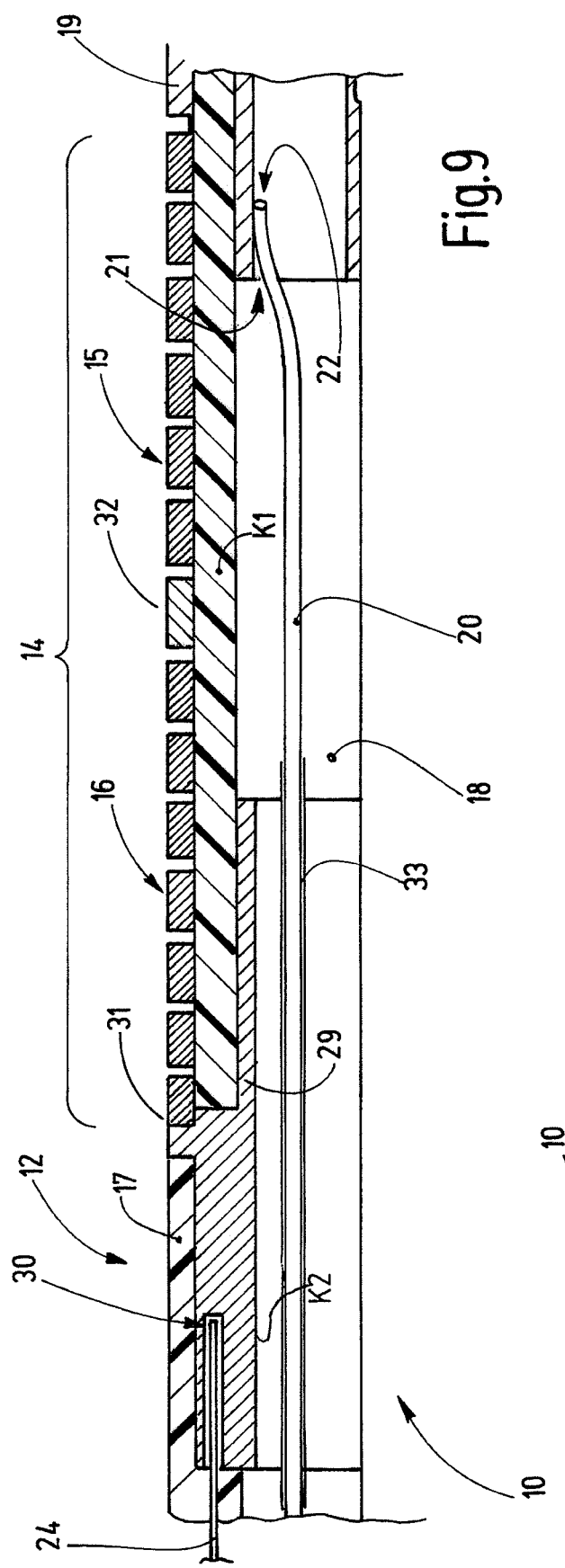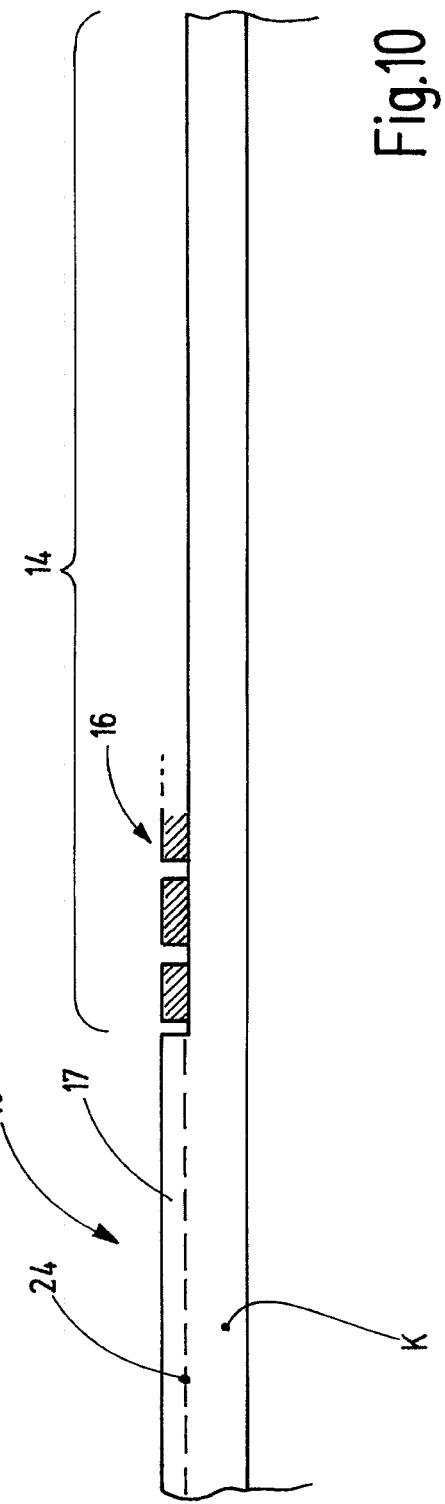

ABLATION PROBE

RELATED APPLICATION(S)

This application claims the benefit of European Patent Application No. 19195658.0, filed Sep. 5, 2019, the contents of which are incorporated herein by reference as if fully rewritten herein.

TECHNICAL FIELD

The invention refers to an ablation probe, particularly a radio frequency (RF) ablation probe with inner cooling, particularly a catheter probe.

BACKGROUND

Radio frequency ablation probes, particularly such of catheter form, have one or two electrodes at their distal end to which a radio frequency voltage is applied in order to heat or coagulate or ablate surrounding tissue when they are inserted in a respective body lumen, e.g. in the liver or lung of a patient. In order to achieve the desired medical treatment effect, the metallic electrode must however remain cool as long as possible, e.g. to heat the tissue extensively as far as possible and to avoid superficial burns of the tissue. For this reason such ablation probes typically comprise a channel through which a cooling fluid is supplied to an inner space extracting heat from the electrodes and diverting it.

From U.S. Pat. No. 6,939,350 B2 such a radio frequency ablation probe is known in which the electrodes are arranged on a multi-lumen hose. It comprises channels for supplying and discharging cooling fluid for cooling the electrodes. In order to guarantee a sufficient heat dissipation, also the hose shall consist of a plastic with a relatively high specific heat conductivity of at least 0.8 W/m*K.

A similar probe is known from WO 03/034932 A1.

For increasing the heat conductivity of plastic it is known from different sources, e.g. DE 85 04 999 U1, DE 29 45 607 A1 and U.S. Pat. No. 3,485,234 A, to include metal inlays in plastic components.

It has, however, shown that increasing the heat conductivity of the hose can have adverse effects.

Starting therefrom it is an object of the invention to provide an improved ablation probe.

SUMMARY

This object is solved with the ablation probe as disclosed herein.

The inventive probe comprises a flexible hose that comprises at least one channel limited by a hose wall and the hose wall thereof is provided with one or more electrodes at a distal end section. The hose wall comprises a higher radial heat conductivity in the distal end section in the radial direction, i.e. in the direction from the electrode toward the channel, as outside of this distal end section.

Due to the higher radial heat conductivity in the distal end section at which the at least one electrode is attached, the heat originating from the electrode is well transferred on the cooling medium and effectively dissipated. On the other hand, the poor heat conductivity of the hose wall outside of the distal end section avoids that body heat of the patient is introduced in the channel of the hose and preheats the cooling fluid. Thus the area of the ablation probe outside of the distal end section can serve as counter current heat exchanger in which the cold cooling fluid exiting out of the distal end section cools cooling fluid inflowing through a fluid conduit, e.g. a capillary tube. The thermal insulation of the probe provided by the low heat conductivity of the material of the hose wall also prevents damage of body tissue or endoscope through cold as it could occur, if the flexible hose would comprise an increased heat conductivity over its total length.

The increased heat conductivity of the hose wall in the distal end section can be effected by different technical measures that can be applied individually or in combination with each other. Particularly the hose wall can have a lower radial thickness in the distal end section as outside of the distal end section. In addition or as an alternative, the hose wall can consist completely or partly of a different plastic in the distal end section as the remaining hose wall, particularly of a plastic with higher heat conductivity.

In addition or as an alternative to each of the measures mentioned above, in the distal end section the hose wall can comprise heat transfer bodies that are embedded in the hose wall. Such heat transfer bodies can be wires, bands or other longitudinal bodies that are arranged extending in circumferential direction and can be, e.g. configured as short sleeves or rings. Such longitudinal heat transfer bodies can also follow a helical line or can be arranged extending in longitudinal direction. Preferably they consist of a heat conducting material, such as copper, silver, aluminum or also steel, particularly stainless steel or carbon fibers. Alternatively, the heat transfer bodies can be irregularly formed and irregularly arranged particles, e.g. wire pieces, fiber pieces, particles, as for example diamond particles, carbon particles or the like.

BRIEF DESCRIPTION OF THE DRAWINGS

Further details of embodiments of the invention are subject of the drawings, the description or claims. The drawings show:

DETAILED DESCRIPTION

Figure 1:
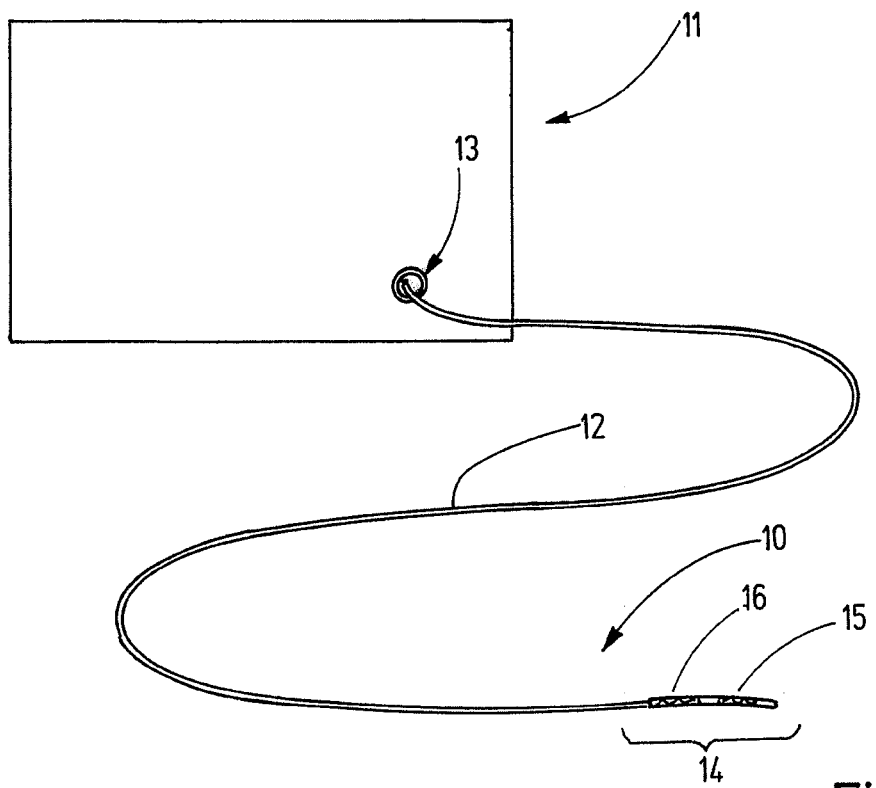
FIG. 1 an inventive probe with a supplying device in a schematical overview illustration, FIG. 2 the probe in a partly longitudinally cut illustration, FIG. 3 the probe according to FIG. 2 in an enlarged partial illustration, FIGS. 4-10 additional embodiments of the probe in a respectively longitudinally cut partly schematic illustration.

An ablation probe 10 is illustrated in FIG. 1 that can be configured in a type of a catheter, for example, in order to be inserted in hollow vessels of a patient, e.g. a hollow vessel of the lung or the liver. The probe 10 is connected to a supplying device 11 that supplies the probe 10 with the necessary operation media, wherein a radio frequency current and a cooling fluid can be part thereof.

The probe 10 consists substantially of a flexible hose 12 that is proximally connected to the device 11 via a suitable connector 13. In distal end section 14 the hose 12 supports at least one or also two electrodes 15, 16 that are electrically connected with a radio frequency generator arranged in the device 11.

Figure 2:
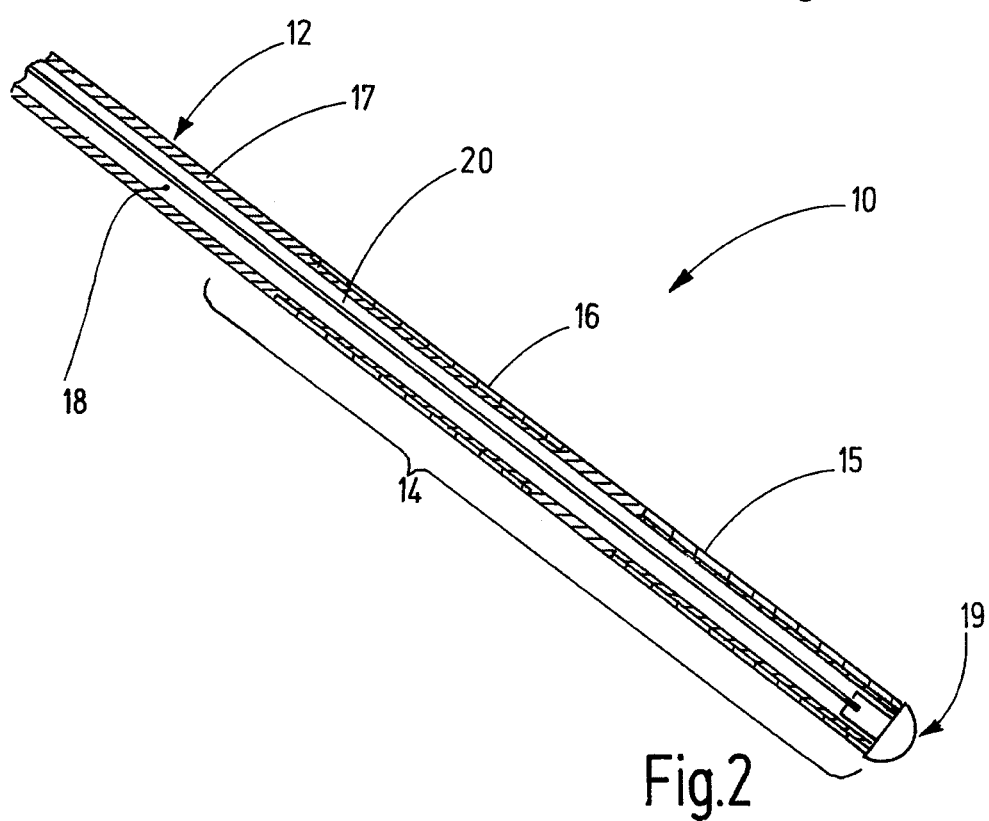

The configuration of probe 10, particularly the distal end section 14 thereof, is apparent from FIGS. 2 and 3. The hose 12 comprises a hose wall 17 that surrounds a channel 18 extending from a proximal end up to the distal end section 14 of the probe 10 and thus the hose wall 17. At the outermost distal end the hose 12 is closed by an end piece 19. The end piece 19 can be configured electrically conductive in order to connect the first electrode 15 with a fluid conduit 20 arranged in the channel 18 and formed by a thin metal tube. The fluid conduit 20 can be a capillary tube, e.g. of stainless steel or another metal that can be connected with a shank of the end piece 19 by a welded connection 21, as shown in FIG. 3.

The fluid conduit 20 comprises a nozzle opening 22 at its end connected with the shank of the end piece 19 via which a cooling media, e.g. $CO_2$, is emitted during operation that is cooled due to expansion and flows back to the device 11 via channel 18 or another non-illustrated outlet opening of the probe 10.

Preferably the hose wall 17 consists of a plastic, particularly a poor heat-conducting plastic, the heat conductivity thereof is low outside the distal end section 14, preferably lower than 0.8 W/m*K. In the area of the two electrodes 15, 16, i.e. in the distal end section 14, the hose wall 17, however, comprises an increased heat conductivity such that the heat resistance in radial direction, i.e. from the electrodes 15, 16 toward the lumen or channel 18, is larger than 0.8 W/m*K. For this the distal end section of the hose wall 17 can consist in the distal end section 14 from another plastic material comprising a better heat conductivity than the remaining part of the hose wall 17. The two different plastic materials are symbolically illustrated in FIG. 3 by different hatches. At a location 23 proximally adjacent to the electrode 16 the hose section forming the distal end section and the remaining hose section are connected with each other, e.g. by gluing or welding or are coupled with each other by an additional short adapter piece arranged in between.

The first plastic K1 of the distal end section as well as the second plastic K2 of the remaining hose wall 17 are flexible. For maintaining the flexibility in the distal end section 14 also the electrodes 15, 16 are flexible, e.g. in that they are formed by a metal band helically bound on the end section 14 of the hose 12. While the first electrode 15 is electrically connected to the fluid conduit 20, an electrical conductor 24 can be provided in the hose wall 17 for a connection of the second electrode 16 with the generator. For example, it can be a conductor extending in axial direction or, if the flexibility shall be increased, a conductor that is arranged in the hose wall 17 following a helical line. Alternatively, one or both electrodes 15 and 16 can be contacted also via wires arranged in channel 18, wherein for this corresponding through holes are required in the hose wall 17 where applicable.

The wall thickness of the hose wall 17 can be reduced in the area of the end section 14, as schematically illustrated in FIG. 3. Alternatively, it can be configured also with a wall thickness equal to the remaining hose wall 17, i.e. without thickness reduction. In that the hose wall 17 is made from a plastic K1 in the end section 14, the specific heat conductivity is (preferably remarkably) higher than the specific heat conductivity of the second plastic K2 of the remaining hose wall, the electrodes 15, 16 are efficiently cooled with low cooling media consumption, whereas the influence of cold along the probe 10 on biological tissue or the endoscope is low outside of the distal end section 14.

The probe 10 described so far operates as follows:

During operation the probe 10 is inserted in a body lumen of a patient. If the distal end section 14 with the electrodes 15, 16 is located at the location to be treated, the electrodes 15, 16 are activated in that the generator of the device 11 applies a radio frequency voltage between the electrodes 15, 16 via the electric conductor 24 and the electrically conductive fluid conduit 20. A current through a contacted biological tissue originates from the electrodes that is heated due to its ohmic resistance and is finally coagulated. Thereby the electrodes 15, 16 are in wet contact to the moist tissue.

Concurrently a cooling fluid, e.g. compacted carbon dioxide, is output at the nozzle opening 22 via the fluid conduit 20 from which it expands into channel 18. It can be subject to an adiabatic cooling and where applicable be subject to additional cooling due to the Joule-Thomson-Effect, wherein temperatures of below −40° C. can be achieved. The temperature gradient between the electrodes 15, 16 and channel 18 created thereby leads to a thermal flow from the electrodes 15, 16 into the channel 18, whereby the electrodes 15, 16 are cooled. In doing so, they remain moist—drying up of tissue due to evaporation of tissue fluid is avoided.

The still cold cooling fluid then flows in the channel 18 in proximal direction and thus counter to the cooling fluid supplied in the fluid conduit. The hose wall 17 then thermically insulates this channel 18 in proximal direction from the surrounding area such that the fluid conduit 20 operates as efficient counter-current heat exchanger and thus pre-cools the cooling fluid before it reaches the nozzle opening 22.

Multiple modifications can be made to the probe described so far. For example, probe 10 can comprise only one single electrode 15, wherein the electrical circuit is then closed via an external large scale counter electrode to be attached to the patient. It is also possible to attach more than two electrodes at the probe 10, e.g. to carry out coagulation along a longer length or in a phased sequence.

It is further possible to configure the hose wall 17 in the distal end section as well as in the remaining section from a uniform plastic, i.e. the plastics K1 and K2 can be the same. In this case the increased heat conductivity of the hose wall 17 in the distal end section is achieved by a reduction of the wall thickness at those locations at which the electrodes 15, 16 are arranged.

The contacting of the electrodes 15, 16 can also be carried out in another alternative manner, as via the fluid conduit 20 and an electrical conductor 24 in the hose wall 17. For example, a contacting of the electrodes via wires or cables in channel 18 is possible. A transfer of current from the lumen of the channel on the external electrodes is then, for example, possible via through holes in the hose wall 17 toward the electrodes or interruptions of the hose wall by electrically conductive adapter pieces. In all embodiments described above or below the fluid conduit 20 can also be equipped with more than one nozzle 22, wherein the nozzles are then preferably configured as radially arranged bores on the distal area of the fluid conduit.

Another modification of the invention is shown in FIG. 4, wherein the above description applies correspondingly for the embodiment according to FIG. 4, apart from the particularities explained in the following on the basis of the already introduced reference numerals. In the distal end section 14 the wall thickness of the hose wall 17 can be reduced. However, it can also be continuously uniformly configured without thickness reduction. In the distal end section 14 a heat transfer body 25 is embedded that can be configured in the present embodiment by a wire embedded in the hose wall 17 following a helical line. The helically formed heat transfer body is limited thereby to the distal end section 14. The remaining hose wall 17 does not contain such a heat transfer body, but at most the electrical conductor 24. In monopolar applications that comprise only one electrode, the electrical conductor 24 can be omitted.

The heat transfer body 25 can be a round wire, a profile wire, a flat wire, a band or the like. For example, it consists from a material having good heat conductivity, such as e.g.

copper, silver, aluminum or also of a still sufficient heat conductive material such as stainless steel. Independent therefrom, instead of a helically formed wounded wire having an arbitrary profile, also one or more rings can be provided that are arranged axially one after the other in series in the hose wall 17. These rings can also have an arbitrary ring cross-section, e.g. a round cross-section, a rectangular cross-section or another profiled cross-section. The heat transfer body 25 consists in this case of multiple individual bodies that are arranged with distance to each other. While the helically formed heat transfer body 25 extends in circumferential direction, as well as in axial direction, the ring-shaped individual heat transfer bodies are exclusively orientated in circumferential direction.

Preferably the heat transfer body 25 of arbitrary configuration is electrically insulated and arranged without contact to the electrodes 15, 16 in the hose wall 17 in all embodiments of the probe 10.

A further embodiment of the inventive probe 10 is apparent from FIG. 5. The embodiment is based on the embodiment according to FIG. 3, the description thereof applies accordingly for the probe according to FIG. 5 on the basis of the already introduced reference numerals. Different to the probe 10 according to FIG. 3 in the distal end section 14 between the two electrodes 15, 16, however, a hose wall section 26 can be provided in addition that consists of the plastic K2 of the remaining hose such that in the distal end section 14 only the hose wall sections supporting the electrodes 15, 16 consist of the plastic K1. This avoids a too strong cold effect on biological tissue between the two electrodes 15, 16, that is of particular importance, if the hose wall intermediate section 26 has a remarkable axial length that is for example at least as long as one fourth of the axial length of an electrode 15 or 16.

Another embodiment of the inventive probe 10 is illustrated in FIG. 6. It is a modification of the probe 10 illustrated in FIG. 4, the description of which applies accordingly for the probe of FIG. 6 with the exception of the particularities explained in the following.

The heat transfer body 25 of the probe according to FIG. 6 comprises two heat transfer body parts 25a, 25b that are arranged respectively only in the area of the electrodes 15, 16. In the intermediate section 27 of the hose wall 17 between the two electrodes 15, 16 heat transfer bodies are omitted. Apart therefrom the probe 10 according to FIG. 6 corresponds to probe 10 of FIG. 4, particularly in terms of the possibilities of configuration of the thickness of the hose wall 17 as well as in terms of the possible configurations of the heat transfer bodies respectively applied on the heat transfer body parts 25a, 25b.

FIG. 7 illustrates a probe 10 for which the description of probe 10 of FIG. 6 applies accordingly apart from the configuration of the heat transfer bodies 25. The heat transfer bodies 25 are here formed by multiplicity of particles 28 embedded in the plastic matrix of the hose walls 17. They consist of a heat conductive material, e.g. metal powder, carbon powder, diamond powder, carbon fibers, wire pieces or the like. The intermediate section 27 between the electrodes 15, 16 is free of such particles 28. The plastic of the end section 14 can be identical to the plastic of the remaining hose wall 17. Alternatively, the remaining hose wall and the intermediate section 27 can consist of a plastic K2 and the particle supporting areas of the end section 14 can consist of the plastic K1.

FIG. 8 illustrates a probe 10 in which the hose wall 17 consists of one and the same plastic K in the end section 14 as well as in the remaining section, wherein the thickness of the hose wall 17 in the end section 14 is initially highly reduced. On this part of the hose wall 17 consisting of plastic K2 a coating of a better heat conductive plastic material K1 is applied, the specific heat conductivity thereof can be increased by any suitable measure. For example, the first plastic K1 can be a plastic having intrinsically better heat conductivity. Alternatively, its heat conductivity can also be increased by embedding of heat transfer bodies 25, e.g. in the form of any of the heat transfer bodies 25 described above or in the form of particles 28. With regard to the configuration of the electrodes as well as their electrical connections, the details apply as described for all embodiments mentioned above with reference to FIGS. 1 to 4, as well as 5.

FIG. 9 illustrates an embodiment of probe 10 in which the end section 14 consists of a thin-walled hose section that is connected with the remaining hose 12 via an adapter, e.g. in the form of a sleeve 29. The sleeve 29 or another adapter extends on one side in the end section 14 and on the other side in the remaining hose 12 in order to connect them in a fluid-type manner. The sleeve is configured from a metal and electrically conductive. It can also be configured from another electrically conductive or also from an electrically insulating material, such as ceramic or plastic.

The hose 12 consists of the plastic K2. The end section 14 can consist of the same or another plastic K1 or K2. This plastic K2 can have the equal or another, particularly a higher specific heat conductivity as the plastic K1. Independent from whether the specific heat conductivity of the plastic K1 is higher, equal or less than the specific heat conductivity of the plastic K2, the end section 14 has however a higher heat conductivity in radial direction than hose 12, if it comprises a smaller wall thickness compared with the hose 12. The wall thickness of the end section 14 can, however, also correspond to the wall thickness of hose 12, wherein the plastic K2 then preferably comprises a higher specific heat conductivity than the plastic K1. The electrical contacting of electrode 16 can be carried out by the sleeve 29. For this the conductor 24 as well as the electrode 16 are electrically connected with the electrically conductive sleeve 29. The conductor 24 can be inserted in a longitudinal bore 30 provided in the wall of sleeve 29 and can be contacted there, e.g. by a deformation of the sleeve or by a spring elastic contact of the conductor 24 against the wall of the longitudinal bore. Alternatively, the conductor 24 can be contacted with the sleeve 29 by welding. The electrode 16 can be connected at a contact location 31 of a flange of the sleeve 29. Between the electrodes 15, 16 a ring-shaped electrically insulating spacer 32 can be arranged. For avoiding electrical short circuits, the fluid conduit 20 comprises at least in the area of the sleeve 29 an electrical insulation 33.

FIG. 10 illustrates an embodiment of probe 10 in which the end section 14 has a reduced wall thickness and thus an increased heat conductivity. Apart therefrom the explanations of the embodiments discussed above apply accordingly.

The inventive probe 10 is particularly usable as radio frequency ablation probe and comprises an inner cooling in order to keep the at least one electrode 15 at the tissue wet and to avoid excessive heating. In the area of the electrode 15 the hose wall 17 of the hose supporting the electrode 15 comprises an increased heat conductivity, whereas apart from that it has a comparably low heat conductivity outside of the electrode carrying distal end section 14. The increase of the heat conductivity in the distal end section 14 can be achieved by reduction of the wall thickness, by selection of a suitable plastic, by arrangement of heat transfer bodies in the hose wall or by a combination of two or more of these features. Customized plastic hoses are, for example, available from the company Mikrolumen or other catheter manufacturing specialists.

LIST OF REFERENCE SIGNS 10 probe
11 device
12 hose
13 connector
14 distal end section of hose 12
15 first electrode
16 second electrode
17 hose wall
18 channel/lumen
19 end piece
20 fluid conduit
21 welded connection
22 nozzle opening
23 connection location in the hose wall 17
24 electrical conductor
25 heat transfer body
25a,b heat transfer body part
26 hose wall intermediate section
27 intermediate section
28 particle
29 sleeve
30 longitudinal bore
31 contact location
32 spacer
33 electrical insulation
K plastic of hose wall
K1 plastic of end section 14
K2 plastic of hose wall outside end section 14

The invention claimed is:

1. A system for radio frequency ablation comprising:
a radio frequency ablation probe (10) with inner cooling, and
an RF generator;
the radio frequency ablation probe (10) with inner cooling comprising:
a flexible hose (12) that comprises a channel (18) limited by a hose wall (17) provided with at least one RF ablation electrode (15) at a distal end section (14) thereof, wherein the at least one RF ablation electrode (15) is configured for heating a tissue adjacent thereto or in contact therewith via application of an RF current;
wherein the at least one RF ablation electrode (15) is connected to an electric conductor (24), wherein the electric conductor (24) is connected to the RF generator for supplying the at least one RF ablation electrode (15) with the RF current;
wherein the hose wall (17) has a higher radial heat conductivity in the distal end section (14) in a radial direction than outside of the distal end section (14);
wherein the distal end section (14) of the flexible hose (12) is connected with a remaining portion of the flexible hose (12) via a sleeve adapter (29);
wherein the sleeve adapter (29) is electrically conductive, and the electric conductor (24) and the at least one RF ablation electrode (15) are each electrically connected to the sleeve adapter (29);
wherein the sleeve adapter (29) comprises an intermediate flange portion between the distal end section (14) of the flexible hose (12) and the remaining portion of the flexible hose (12) to which the at least one RF ablation electrode is electrically connected;
wherein the intermediate flange portion has a diameter substantially equal to a diameter of the remaining portion of the flexible hose (12) and larger than a diameter of the distal end section (14) of the flexible hose (12) such that the diameter of the intermediate flange portion is substantially equal to a diameter of the at least one RF ablation electrode.

2. The system according to claim 1, wherein the hose wall (17) is made of plastic (K, K1, K2).

3. The system according to claim 2, wherein the hose wall (17) comprises a first plastic (K1) in the distal end section (14) and a second plastic (K2) separate from the first plastic (K1).

4. The system according to claim 3, wherein the first plastic (K1) has a lower specific heat resistance than the second plastic (K2).

5. The system according to claim 1, wherein the hose wall (17) comprises at least one heat transfer body (25) in the distal end section (14).

6. The system according to claim 5, wherein the at least one heat transfer body (25) is embedded in the hose wall (17).

7. The system according to claim 5 wherein the at least one heat transfer body (25) is one of a wire comprising a metal, a band comprising a metal, or a group of rings or sleeves.

8. The system according to claim 5, wherein the at least one heat transfer body (25) is arranged in a manner extending in a circumferential direction and/or in a longitudinal direction.

9. The system according to claim 5, wherein multiple heat transfer bodies (25a, 25b, 28) are provided.

10. The system according to claim 9, wherein the heat transfer bodies (25a, 25b, 28) are irregularly arranged and/or are irregularly formed particles.

11. The system according to claim 1, wherein the hose wall (17) has a wall thickness at the distal end section (14) that is smaller than the wall thickness of the hose wall (17) in a section of the hose wall outside of the distal end section.

12. The system according to claim 1, wherein a fluid conduit (20) ending in the distal end section (14) of the flexible hose (12) is arranged in the channel (18).

13. The system according to claim 12, wherein the fluid conduit (20) is configured as a metallic capillary tube.

14. The system according to claim 1, wherein the flexible hose (12) comprises the electric conductor (24) that is connected with the at least one RF ablation electrode (15, 16).

15. A radio frequency ablation probe (10) with inner cooling, comprising:
a flexible hose (12) that comprises a channel (18) limited by a hose wall (17) provided with at least one RF ablation electrode (15) at a distal end section (14) thereof, wherein the at least one RF ablation electrode (15) is configured for heating a tissue adjacent thereto or in contact therewith via application of an RF current;
wherein the at least one RF ablation electrode (15) is connected to an electric conductor (24), wherein the electric conductor (24) is configured to be connected to an RF generator for supplying the at least one RF ablation electrode (15) with the RF current;
wherein the hose wall (17) has a higher radial heat conductivity in the distal end section (14) in a radial direction than outside of the distal end section (14);

wherein the distal end section (14) of the flexible hose (12) is connected with a remaining portion of the flexible hose (12) via a sleeve adapter (29);

wherein the sleeve adapter (29) is electrically conductive, and the electric conductor (24) and the at least one RF ablation electrode (15) are each electrically connected to the sleeve adapter (29);

wherein the sleeve adapter (29) comprises an intermediate flange portion between the distal end section (14) of the flexible hose (12) and the remaining portion of the flexible hose (12) to which the at least one RF ablation electrode is electrically connected;

wherein the intermediate flange portion has a diameter substantially equal to a diameter of the remaining portion of the flexible hose (12) and larger than a diameter of the distal end section (14) of the flexible hose (12) such that the diameter of the intermediate flange portion is substantially equal to a diameter of the at least one RF ablation electrode.

16. The probe of claim 15, wherein the sleeve adapter (29) comprises a longitudinally-oriented bore in which the electric conductor (24) is received, wherein the electric conductor (24) is in electrical contact with a wall of the longitudinally-oriented bore.

17. The probe of claim 15, further comprising a fluid conduit (20) that extends longitudinally in the channel (18) and through the sleeve adapter (29) and that terminates in the distal end section (14) of the flexible hose (12);

wherein the fluid conduit (20) comprises a metallic capillary tube;

wherein electrical insulation is disposed about at least a portion of the metallic capillary tube that extends through the sleeve adapter (29).

* * * * *